(12) United States Patent
Marenick

(10) Patent No.: US 7,094,415 B2
(45) Date of Patent: Aug. 22, 2006

(54) SKIN CARE PRODUCTS CONTAINING WHOLE EGG

(75) Inventor: Michael Marenick, Glen Ridge, NJ (US)

(73) Assignee: L'Avenir, LLC, Fairfield, NJ (US)

( * ) Notice: Subject to any disclaimer, the term of this patent is extended or adjusted under 35 U.S.C. 154(b) by 91 days.

(21) Appl. No.: 10/260,344

(22) Filed: Oct. 1, 2002

(65) Prior Publication Data

US 2003/0133989 A1    Jul. 17, 2003

Related U.S. Application Data

(63) Continuation of application No. 10/039,793, filed on Jan. 8, 2002, now abandoned.

(60) Provisional application No. 60/298,874, filed on Jun. 18, 2001.

(51) Int. Cl.
*A61K 9/00* (2006.01)
*A61K 6/00* (2006.01)
*A61K 7/00* (2006.01)

(52) U.S. Cl. ..................... 424/401; 424/400

(58) Field of Classification Search ............... 424/401, 424/400
See application file for complete search history.

(56) References Cited

U.S. PATENT DOCUMENTS 4,223,018 A * 9/1980 Belle .......................... 514/2
4,382,967 A * 5/1983 Koshida et al. ............... 426/96

FOREIGN PATENT DOCUMENTS

FR    2538248    *  7/1984

OTHER PUBLICATIONS

Berkow et al., The Merck Manual of Medical Information, p. 1303, 1997.*
Lactoferrin DMV International Nutritionals.*
MSM, Reach4 Life Quality Products, 1999.*
Merck Index, 11th ed., 1989, monograph 301.*

* cited by examiner

*Primary Examiner*—San-Ming Hui
(74) *Attorney, Agent, or Firm*—Dan M. De La Rosa

(57) ABSTRACT

The present invention provides a skin care product comprising whole egg, an emollient substance and a humectant substance, colostrum, lactoferrin and/or methyl sulfonyl methane (MSM).

20 Claims, No Drawings

SKIN CARE PRODUCTS CONTAINING WHOLE EGG

RELATED APPLICATION

This application is a continuation of U.S. application Ser. No. 10/039,793, entitled HYDROLYZED WHOLE EGG PRODUCTS & RELATED METHODS, which was filed on Jan. 8, 2002 now abandoned and is related to Provisional U.S. Application Ser. No. 60/298,874, entitled A SKIN CARE PRODUCT AND A METHOD OF PRODUCING SAME which was filed on Jun. 18, 2001.

BACKGROUND OF THE INVENTION

1. Field of the Invention

This invention relates to a skin care product containing whole eggs wherein the eggs are utilized as a carrier of the active ingredients in the product and is used to achieve the desired effects of the product. More specifically, the present invention relates to a whole egg product for use as a cosmetic, pharmaceutical and/or medicinal product applicable for soothing sore muscles, expediting the healing and repairing process of the skin and reducing the visual appearance of cellulite.

2. Description of the Related Art

There are numerous cosmetic and skin care products that use components of eggs as major ingredients in their formulation. For example, some cosmetic or skin care products use egg whites in their formulation. Other cosmetic and skin care products use extracts of yokes in their formulation. The use of whole egg has never been achieved since the mixing and/or shearing process of the manufacturing of the product will cause the egg components to coagulate and form mayonnaise. There have also been problems with incorporating the whole egg in the formations since the shearing and heating process of most processes have denatured the proteins in the eggs and have inactivated the active ingredients in the egg which provides for its excellent carrier/delivery properties. In addition, there are no cosmetic, medicinal, pharmaceutical and/or cosmopharmaceutical product that utilize whole eggs as carriers for their active ingredients.

SUMMARY OF THE INVENTION

In one embodiment, the present invention relates to a formulation comprising at least one whole egg, at least one emollient substance and at least one humectant substance. The term whole egg is defined as the egg white and the yolk, which through a special process has had the water extracted from it. For purposes of this invention, the term emollient substance is defined as any natural or synthetic oil and their compound equivalents. The term humectant substance for the purposes of this invention is defined as glycerin and/or any other chemical of natural or synthetic origin. In another embodiment, the humectant substance is selected from a group consisting of glycerin, butylenes glycol, propylene glycol, pentylene glycol and mixtures thereof. In yet another embodiment, the emollient substance is selected from a group consisting of *Prunus Amygdalus Dulis* (Sweet Almond) Oil, Squalene, *Prunus Armeniaca* (Apricot) Kernel Oil, *Carthamus Tinetorius* (Safflower) Oil, *Helianthus Annuus* (Sunflower) Seed Oil and extracts thereof and mixtures thereof. In still another embodiment, the formulation can be utilized as a cosmetic, cosmopharmaceutical and pharmaceutical formulation.

In a further embodiment, the present invention relates to a formulation comprising: egg and lactoferrin and/or colostrum. In still a further embodiment, the present invention provides for a formulation comprising: egg, at least one emollient substance, at least one humectant substance, and lactoferrin and/or colostrum. In still another embodiment, the colostrum is bovine colostrum.

In yet a further embodiment, the present invention relates to a formulation comprising whole egg and methyl sulfonyl methane (MSM). In still yet a further embodiment, the formulation comprises whole egg, at least one emollient substance, at least one humectant substance, and methyl sulfonyl methane (MSM). In a further embodiment, the present invention provides a formulation comprising egg, methyl sulfonyl methane (MSM) and lactoferrin and/or colostrum. In another further embodiment, the formulation comprises: whole egg, at least one emollient substance, at least one humectant substance, methyl sulfonyl methane (MSM) and lactoferrin and/or colostrum. In still another embodiment, the colostrum is bovine colostrum.

In still yet another formulation, the present invention relates to a cellulite formulation comprising at least one whole egg, at least one emollient substance, at least one humectant substance and at least one aromatherapeutical substance. In a further embodiment, the humectant substance is selected from a group consisting of glycerin, butylenes glycol, propylene glycol, pentylene glycol and mixtures thereof. In yet a further embodiment, the emollient substance is selected from a group consisting of *Prunus Amygdalus Dulis* (Sweet Almond) Oil, Squalene, *Prunus Armeniaca* (Apricot) Kernel Oil, *Carthamus Tinetorius* (Safflower) Oil, *Helianthus Annuus* (Sunflower) Seed Oil and extracts thereof and mixtures thereof.

In still yet a further embodiment, the aromatherapeutical substance is selected from a group consisting of *Lavendula Angustifolia* (Lavender) oil, *Geranium Maculatum* Oil, *Citrus Grandis* (Grapefruit) oil, *Juniperus Communis* Oil, *Pimenta Acris* (Bay) Oil, *Lavendula Hybrida, Geranium Robertianum, Geranium Thunbergil, Citrus Aurantium Dulsis* (Orange) Oil, *Citrus Nobilis* (Mandarin Orange) Oil, *Citrus Limonum* (Lemon) Oil and extracts thereof and mixtures thereof. For purposes of this invention, the term aromatherapeutical substance is defined as a combination of pure essental oils with aromatic properties.

In another further embodiment, the present invention relates to skin care formulation comprising at least one whole egg, at least one emollient substance, at least one humectant substance and at least one skin nourishing/wound healing substance. In still another further embodiment, the humectant substance is selected from a group consisting of glycerin, butylenes glycol, propylene glycol, pentylene glycol and mixtures thereof. In yet another further embodiment, the emollient substance is selected from a group consisting of *Prunus Amygdalus Dulis* (Sweet Almond) Oil, Squalene, *Prunus Armeniaca* (Apricot) Kernel Oil, *Carthamus Tinetorius* (Safflower) Oil, *Helianthus Annuus* (Sunflower) Seed Oil and extracts thereof and mixtures thereof.

In still yet another further embodiment, the skin nourishing/wound healing substance is selected from a group consisting of aloe barbadensis leaf juice, white willow bark, and extracts thereof and mixtures thereof. The term skin nourishing/wound healing substance is defined as any material that will assist in or promote the skin healing and/or normalizing process. In another embodiment, the skin care formulation further comprises an acne drug and the formulation functions as an acne formulation. In still another embodiment, the active drug is salicylic acid.

In a further embodiment, the present invention also relates to a muscle soothing formulation comprising at least one whole egg, at least one emollient substance, at least one humectant substance and a muscle soothing substance. In still a further embodiment, the humectant substance is selected from a group consisting of glycerin, butylenes glycol, propylene glycol, pentylene glycol and mixtures thereof. In yet a further embodiment, the emollient substance is selected from a group consisting of *Prunus Amygdalus Dulis* (Sweet Almond) Oil, Squalene, *Prunus Armeniaca* (Apricot) Kernel Oil, *Carthamus Tinetorius* (Safflower) Oil, *Helianthus Annuus* (Sunflower) Seed Oil and extracts thereof and mixtures thereof.

In still yet a further embodiment, the muscle soothing substance comprises a blend of Menthol, *Methyl Salicylate, Eucalyptus Globulus* Oil, Camphor, and *Mentha Piperita* (Peppermint) Oil. For purposes of this invention, the muscle soothing substance is defined as any active ingredient or pure substance that can penetrate and cause sensation to the muscle tissue.

In another further embodiment, the present invention relates to a whole egg formulation manufactured by a method comprising: shearing a mixture of water, triethanolamine, glycerin and methyl paraben and heating the mixture to a temperature from about 70 degrees Celsius to about 80 degrees Celsius; adding sweet almond oil, stearic acid, glyceryl stearate, and propylparaben to the mixture and shearing and heating the entire mixture to a temperature from about 90 degrees Celsius to about 100 degrees Celsius; adding a egg to the oil phase of the entire mixture while stopping the heating process and adding the oil phase to the water phase to form an emulsion; and upon formation of the emulsion, cooling the entire formulation.

In still another further embodiment, the method further comprising adding additional substances to said formulation during said cooling process. In yet another further embodiment, the formulation made by the above method may be utilized as a cosmetic, cosmopharmaceutical and pharmaceutical formulation depending on what additional substance(s) are added to the formulation during the cooling process.

In another embodiment, the present invention relates to a skin care formulation manufactured by a process comprising: shearing a mixture of water, triethanolamine, trisodium EDTA, glycerin and methyl paraben and heating the mixture to a temperature from about 70 degrees Celsius to about 80 degrees Celsius; adding cetearyl alcohol, sweet almond oil, cetyl alcohol, stearic acid, glyceryl stearate, sorbitan stearate, tocopherol, retinyl palmitate, tetrahexyldecyl ascorbate and propylparaben to the mixture and shearing and heating the entire mixture to a temperature from about 90 degrees Celsius to about 100 degrees Celsius; adding a egg to the oil phase of the entire mixture while stopping the heating process and adding the oil phase to the water phase to form an emulsion; upon formation of the emulsion, cooling the entire formulation; and adding glycerin, salicylic acid and phenoxyethyanol and shearing the entire formulation. In still another embodiment, the formulation made by the above process may be used for acne skin care.

In yet another embodiment, the present invention further relates to a muscle soothing formulation manufactured by a process comprising: shearing a mixture of water, triethanolamine, glycerin, trisodium and methyl paraben and heating the mixture to a temperature from about 70 degrees Celsius to about 80 degrees Celsius; adding sweet almond oil, cetearyl alcohol, stearic acid, glyceryl stearate, cetyl lactate, tocopherol, retiryl palmitate, tetrahexyldecyl ascorbate and propylparaben to the mixture and shearing and heating the entire mixture to a temperature from about 90 degrees Celsius to about 100 degrees Celsius; adding a egg to the oil phase of the entire mixture while stopping the heating process and adding the oil phase to the water phase to form an emulsion; upon formation of the emulsion, cooling the entire formulation; and adding cyclomethicone, menthol, methyl salicylate, eucalyptus globules oil, camphor, peppermint oil, pheroxyethanol and chlorophyll and shearing the entire formulation.

In a further embodiment, the present invention relates to a cellulite formulation manufactured by a process comprising: shearing a mixture of water, triethanolamine, glycerin, propylene glycol and methyl paraben and heating the mixture to a temperature from about 70 degrees Celsius to about 80 degrees Celsius; adding sweet almond oil, cetyl lactate, stearic acid, paraffin, sorbitan stearate, glyceryl stearate, cyclomethicone and dimethicone copotyol, and propylparaben to said mixture and shearing and heating the entire mixture to a temperature from about 90 degrees Celsius to about 100 degrees Celsius; adding a egg to the oil phase of the entire mixture while stopping the heating process and adding the oil phase to the water phase to form an emulsion; upon formation of the emulsion, cooling the entire formulation; and adding grapefruit oil, lavender oil, *geranium maculatum* oil, *juniperus communis* oil, cumen extract, *sambucus nigra* extract, caraway extract, sage extract, parsley extract, *primula veris* extract and phenoxyethanol and shearing the entire formulation.

In still a further embodiment, the present invention relates to a method of manufacturing a formulation, the method comprising: shearing at least one emollient substance and at least one humectant substance; adding at least one whole egg to the oil phase of the mixture and then adding the oil phase to the water phase to form an emulsion; and upon formation of the emulsion, cooling the formulation. In yet a further embodiment, the humectant substance is selected from a group consisting of glycerin, butylenes glycol, propylene glycol, pentylene glycol and mixtures thereof. In yet another further embodiment, the emollient substance is selected from a group consisting of *Prunus Amygdalus Dulis* (Sweet Almond) Oil, Squalene, *Prunus Armeniaca* (Apricot) Kernel Oil, *Carthamus Tinetorius* (Safflower) Oil, *Helianthus Annuus* (Sunflower) Seed Oil and extracts thereof and mixtures thereof. In still yet a further embodiment, the formulation may be used as a cosmetic, cosmopharmaceutical and pharmaceutical formulation depending on what additional substance(s) are added to the formulation.

DETAILED DESCRIPTION OF THE INVENTION

As required, detailed embodiments of the present invention are disclosed herein; however, it is to be understood that the disclosed embodiments are merely exemplary of the invention that may be embodied in various forms. The figures are not necessary to scale, some features may be exaggerated to show details of particular components. Therefore, specific structural and functional details disclosed herein are not to be interpreted as limiting, but merely as a basis for the claims and as a representative basis for teaching one skilled in the art to variously employ the present invention.

The present invention provides cosmetic, cosmopharmaceutical and pharmaceutical formulations containing whole egg(s). Whole eggs are a great source of nutrients and function as carriers/deliverers of various active and inactive ingredients to the respective human/animal bodily components, organs, tissues, cells, etc. The present invention utilizes chicken eggs but can use any and all types of eggs, including but not limited to, poultry and reptile eggs.

The formulation of the present invention includes, but is not limited to, a skin care formulation, a muscle soothing formulation and a cellulite formulation. There are three unique products, discussed in detail below, that have radically different functions ranging from soothing sore muscles, to expediting the repairing process of the skin and reducing the visual appearance of cellulite. The common factor that is shared by all of these products is the use of the whole egg to achieve the desired effects in each case and the unique processing method of incorporating the egg within the formulation and allowing the whole egg to act as a carrier of the active ingredients in each case.

The specific examples below will enable the present invention to be better understood. However, they are given merely by way of guidance and do not imply any limitation to this invention.

EXAMPLE 1

HEALFAST" Skin Care Formulation

The skin care formulation of the present invention is designed to treat eczema, psoriasis, sunburns, razor bums, blisters, acne, insect bites, burns, cuts, bruises and dry skin. The skin care formulation of the present invention, may be manufactured by the following process: shearing a mixture of water, triethanolamine, trisodium EDTA, glycerin and methyl paraben and heating the mixture to a temperature from about 70 degrees Celsius to about 80 degrees Celsius; adding cetearyl alcohol, sweet almond oil, cetyl alcohol, stearic acid, glyceryl stearate, sorbitan stearate, tocopherol, retinyl palmitate, tetrahexyldecyl ascorbate and propylparaben to the mixture and shearing and heating the entire mixture to a temperature from about 90 degrees Celsius to about 100 degrees Celsius; adding a egg to the oil phase of the entire mixture while stopping the heating process and adding the oil phase to the water phase to form an emulsion; upon formation of the emulsion, cooling the entire formulation; and adding glycerin, salicylic acid and phenoxyethyanol and shearing the entire formulation. Table 1 below indicates the ingredients of the skin care product of the present invention including the sequence of addition into the formulation and the % W/W of each ingredient relate to the entire formulation.

TABLE 1

Skin Care Ingredients for HEALFAST" Formulation

| SEQUENCE | TRADENAME | INCI NAME | % W/W |
|---|---|---|---|
| 1 | Water | Water (Aqua) | 50–80 |
| 1 | Triethanolamine 99% | Triethanolamine | 0.05–5.00 |
| 1 | Hampene Na3T | Trisodium EDTA | 0.10–1.00 |
| 1 | Glycerin | Glycerin | 0.10–3.00 |
| 1 | Methylparaben | Methylparaben | 0.10–5.00 |
| 2 | Lipowax D | Cetearyl Alcohol (and) Ceteareth–20 | 0.10–5.00 |
| 2 | Sweet Almond Oil | Sweet Almond (*Prunus Amygdalus Dulcis*) Oil | 0.10–10.00 |
| 2 | Lipocol | Cetyl Alcohol | 0.10–5.00 |
| 2 | Stearic Acid XXX | Stearic Acid | 0.10–5.00 |
| 2 | Lipomulse 165 | Glyceryl Stearate (and) PEG-100 Stearate | 0.10–5.00 |

TABLE 1-continued

Skin Care Ingredients for HEALFAST" Formulation

| SEQUENCE | TRADENAME | INCI NAME | % W/W |
|---|---|---|---|
| 2 | Sorbitan Stearate | Sorbitan Stearate | 0.10–5.00 |
| 2 | Covi–ax T–50 | Tocopherol | 0.01–1.00 |
| 2 | Vitamin A Palmitate | Retinyl Palmitate | 0.10–3.00 |
| 2 | BVOSC (Barnet) | Tetrahexyldecyl Ascorbate | 0.10–3.00 |
| 2 | Propylparaben | Propylparaben | 0.10–3.00 |
| 2 | Hydrolyzed Whole Egg | Hydrolyzed Whole Egg | 0.10–10.00 |
| 3 | Glycerin | Glycerin | 0.10–5.00 |
| 3 | Salicylic Acid | Salicylic Acid | 0.01–0.49 |
| 4 | Emmeressence 1160 Rose | Phenoxyethyanol | 0.10–3.00 |

In another embodiment of the present invention, the above skin care formulation (HEALFAST") may be embedded or incorporated onto a patch or bandage, which can be adhered onto the target area of the human body (for example, a cut or laceration on the forearm). The patch or bandage may be of any shape or size and it comprises an adhesive strip for attaching the pad or bandage onto the human user and a pad containing the skin care formulation, which is placed directly upon the target area. The patch or bandage may further comprise removable tabs (which are removed at the moment of use) and a sterile wrapper or packaging.

The skin care formulation may be embedded or incorporated onto or into the pad through any and all techniques utilized in embedding medicament, ointment or other substances. The pad and adhesive strip may be constructed of any stretchable, bendable or breathable material, including various fabrics. The pad and adhesive strip may also be constructed of water resistant materials. The pad may be an absorbent cushion pad that has excellent drainage properties. The patch or bandage may be dermatologically tested and hypoallergenic.

In still another embodiment, the muscle soothing formulation and cellulite formulation discussed below may also be embedded or incorporated onto patches or bandages. Like the HEALFAST" patches or bandages, the muscle soothing and cellulite patches or bandages may also be attached onto the target area of the human anatomy (for example, the cellulite patch may be placed upon the woman s thighs or the muscle soothing patch may be adhered to an aching back or foot). The patches may also contain concentrated amount of the formulation and based upon the formulation, the patch or bandage may be designed to be used for hours or for days and even, for weeks. The patches or bandages are utilized to apply the formulation directly onto target areas and may provide a less messy alternative to direct application of the formulation onto the user s body. The patches will also prevent contact of the formulation with the user s clothing.

EXAMPLE 2

ULTRA SOOTHE" Muscle Soothing Formulation

The muscle soothing formulation of the present invention is designed to treat muscle aches and pains, and is applicable for all muscle parts and joints. The muscle soothing formulation of the present invention may be manufactured by the following method: shearing a mixture of water, triethanolamine, glycerin, trisodium and methyl paraben and heating the mixture to a temperature from about 70 degrees Celsius to about 80 degrees Celsius; adding sweet almond oil, cetearyl alcohol, stearic acid, glyceryl stearate, cetyl lactate, tocopherol, retiryl palmitate, tetrahexyldecyl ascorbate and propylparaben to the mixture and shearing and heating the entire mixture to a temperature from about 90 degrees Celsius to about 100 degrees Celsius; adding a egg to the oil phase of the entire mixture while stopping the heating process and adding the oil phase to the water phase to form an emulsion; upon formation of the emulsion, cooling the entire formulation; and adding cyclomethicone, menthol, methyl salicylate, eucalyptus globules oil, camphor, peppermint oil, pheroxyethanol and chlorophyll and shearing the entire formulation. Table 2 below indicates the ingredients of the muscle soothing product of the present invention including the sequence of addition into the formulation and the % W/W of each ingredient relate to the entire formulation.

TABLE 2

Muscle Soothing Ingredients for ULTRA SOOTHE" Formulation

| SEQUENCE | TRADENAME | INCI NAME | % W/W |
|---|---|---|---|
| 1 | Water | Water (Aqua) | 20–60 |
| 1 | Glycerin | Glycerin | 0.10–10.00 |
| 1 | Methylparaben | Methylparaben | 0.10–0.30 |
| 1 | Hampene Na3T | Trisodium EDTA | 0.10–0.30 |
| 1 | Triethanolamine | Triethanolamine | 0.01–3.00 |
| 2 | Stearic Acid | Stearic Acid | 0.50–5.00 |
| 2 | Lipowax D | Cetearyl Alcohol (and) Ceteareth–20 | 2.50–7.50 |
| 2 | Almond Oil | Sweet Almond (*Prunus Amygdalus Dulcis*) Oil | 5.0–15.00 |
| 2 | Lipomulse 165 | Glyceryl Stearate (and) PEG–100 Stearate | 3.50 |
| 2 | Ceraphyl 28 | Cetyl Lactate | 0.30–4.00 |
| 2 | Hydrolyzed Whole Egg | Hydrolyzed Whole Egg | 0.10–10.00 |
| 2 | Covi-ax T-50 | Tocopherol | 0.10–0.50 |
| 2 | Vitamin A Palmitate | Retinyl Palmitate | 0.10–0.50 |
| 2 | BVOSC (Barnet) | Tetrahexyldecyl Ascorbate | 0.10–1.00 |
| 2 | Propylparaben | Propylparaben | 0.10–0.30 |
| 3 | Sepigel 305 | Polyacrylamide (and) C13–14 Isoparaffin (and) Laureth-7 | 2–5 |
| 4 | Dow Corning 345 Fluid | Cyclomethicone | 1.00–5.00 |
| 5 | Menthol | Menthol | 2–10 |
| 5 | Methyl Salicylate | Methyl Salcylate | 2–10 |
| 5 | Eucalyptus Oil | *Eucalyptus Globulus* Oil | 0.10–5.00 |
| 5 | Camphor | Camphor | 2–10 |
| 5 | Peppermint Oil | Peppermint (*Mentha Piperita*) Oil | 0.10–5.00 |
| 6 | Emmeressence 1160 Rose | Phenoxyethyanol | 0.10–3.00 |
| 7 | Chlorophyllin Coper Complex | Chlorophyll | q.s. |

EXAMPLE 3

CELLUTONE" Cellulite Formulation

The cellulite formulation of the present invention is designed to reduce the visual appearance of cellulite. The cellulite formulation of the present invention may be manufactured by the following method: shearing a mixture of water, triethanolamine, glycerin, propylene glycol and methyl paraben and heating the mixture to a temperature from about 70 degrees Celsius to about 80 degrees Celsius; adding sweet almond oil, cetyl lactate, stearic acid, paraffin, sorbitan stearate, glyceryl stearate, cyclomethicone and dimethicone copotyol, and propylparaben to said mixture and shearing and heating the entire mixture to a temperature from about 90 degrees Celsius to about 100 degrees Celsius; adding a egg to the oil phase of the entire mixture while stopping the heating process and adding the oil phase to the water phase to form an emulsion; upon formation of the emulsion, cooling the entire formulation; and adding grapefruit oil, lavender oil, *geranium maculatum* oil, *juniperus communis* oil, cumen extract, *sambucus nigra* extract, caraway extract, sage extract, parsley extract, *primula veris* extract and phenoxyethanol and shearing the entire formulation. Table 3 below indicates the ingredients of the cellulite product of the present invention including the sequence of addition into the formulation and the % W/W of each ingredient relate to the entire formulation.

TABLE 3

Cellulite Ingredients for CELLUTONE" Formulation

| SEQUENCE | TRADENAME | INCI NAME | % W/W |
|---|---|---|---|
| 1 | Water | Water (Aqua) | 40–60 |
| 1 | Triethanolamine 99% | Triethanolamine | 0.30–3.00 |
| 1 | Carbowax 400 | PEG–8 | 0.10–10.00 |
| 1 | Glycerin | Glycerin | 0.50–5.00 |
| 1 | Propylene Glycol | Propylene Glycol | 1.00–4.00 |
| 1 | Methylparaben | Methylparaben | 0.10–1.00 |
| 2 | Lipo GMS 450 | Glyceryl Stearate | 0.25–5.00 |
| 2 | Sweet Almond Oil | Sweet Almond (*Prunus Amygdalus Dulcis*) Oil | 0.60–6.00 |
| 2 | Ceraphyl 28 | Cetyl Lactate | 0.50–5.00 |
| 2 | Stearic Acid XXX | Stearic Acid | 0.50–5.00 |
| 2 | Paraffin | Paraffin | 0.50–5.00 |
| 2 | Sorbitan Stearate | Sorbitan Stearate | 0.50–5.00 |
| 2 | Propylparaben | Propylparaben | 0.10–5.00 |
| 2 | Dow Corning 3225C | Cyclomethicone (and) Dimethicone Copotyol | 0.10–10.00 |
| 2 | Hydrolyzed Whole Egg | Hydrolyzed Whole Egg | 0.10–10.00 |
| 3 | Grapefruit Oil | Grapefruit (*Citrus Gandis*) Oil | 0.10–2.00 |
| 3 | Lavender Oil | Lavender (*Lavendula Angustifoli*) Oil | 0.50–5.00 |
| 3 | Geranium Oil | *Geranium Maculatum* Oil | 0.50–5.00 |
| 3 | Juniperberry Oil | *Juniperus Communis* Oil | 0.50–5.00 |
| 4 | Cumin Extract | Cumin (*Cuminum Cyminum*) Extract | 0.50–5.00 |
| 4 | Elderflower Extract | *Sambucus Nigra* Extract | 0.50–5.00 |
| 4 | Caraway Extract | Caraway (*Carum Carvi*) Extract | 0.50–5.00 |
| 4 | Sage Extract | Sage (*Salvia Officinalis*) Extract | 0.50–5.00 |
| 4 | Parsley Extract | Parsley (*Carum Petroselinum*) Extract | 0.50–5.00 |
| 4 | Cowslip Extract | *Primula Veris* Extract | 0.50–5.00 |
| 5 | Emmeressence 1160 Rose | Phenoxyethyanol | 0.10–3.00 |

Below is a manufacturing process that is suitable for all three products which depicts a unique method of the addition of the water-soluble egg into the oil phase of the formulation at relatively high temperatures. The process allows the egg to encapsulate the oils and permits the formulation containing the encapsulated egg to penetrate into the skin and deliver the active ingredients. The egg with the encapsulated oils is termed Eggosomes and is formed prior to the emulsification process.

The manufacturing process of the present invention is applicable to Examples 1–3 of the present invention and relates to the ingredients and sequence of additions illustrated in Tables 1–3. The manufacturing procedure is as follows:

Into a stainless steel, jacketed kettle equipped with at least one high shear mixer and at least one planetary mixer, Sequence #1 is loaded under adequate shear and heated from about 76 degrees Celsius to about 78 degrees Celsius. (For purposes of this invention, adequate shear is defined as from about 800 to about 2000 RPMs).

After adequate shearing and heating of Sequence #1, Sequence #2 is then loaded into the kettle and is further heated from about 82 degrees Celsius to about 86 degrees Celsius, with adequate shear. (For purposes of this invention, adequate shear is defined as from about 800 to about 2000 RPMs).

When the kettle reaches its optimum temperatures, the whole egg is added to the oil phase kettle and the heating is stopped. The egg is gently stirred into the oil, and is evenly coated with the oil, but not burned (this is known as the formation of the Eggosome). Within seconds, the oil phase is added to the water phase, thus completing the Eggosome or carrier vehicle. The emulsion is formed. The temperature and energy are carefully monitored to ensure that a small particle is formed (this can be confirmed under the microscope).

Once the emulsion is formed, the cooling process begins and the process may then be continued until the phases of the formula are further added.

The Eggosome or Ovasome of the present invention is capable of carrying and delivering any and all types of ingredients, active and inactive, natural and synthetic, drugs, nutrients, or bioactives. The formulation of the present invention can also be modified to function as a cosmetic and/or pharmaceutical formulation depending on the additional ingredients added to this unique manufacturing process and depending on what ingredients may be desired to be delivered to a human or animal target. In one embodiment, the formulation of the present invention may be simply applied to the skin and the semi-permeable nature of the skin will allow entrance of the formulation and the Eggosome or Ovasome will then be able to deliver the desired material to the desired target. Since the Eggosome or Ovasome is capable of carrying various ingredients including active drugs, the formulation of the present invention may also have medicinal applications. The present invention may also include accelerated healing ingredients that may be applied to adhesive patches and bandages for commercial and hospital use.

Numerous modifications and variations of the present invention are possible in light of the above teachings. It is therefore to be understood that within the scope of the attendant claims attached hereto, this invention may be practiced otherwise than as specifically disclosed herein.

What is claimed is:

1. A skin care product comprising at least one humectant substance, at least one emollient substance, colostrum and at least one whole egg, said whole egg selected from a group consisting of chicken eggs, reptile eggs and mixtures thereof, said whole egg having water extracted from it, said humectant substance is selected from a group consisting of glycerin, butylenes glycol, propylene glycol, pentylene glycol and mixtures thereof, said emollient substance is selected from a group consisting of *Prunus Amygdalus Dulcis* Oil, *Squalene, Prunus Armeniaca Kernel* Oil, *Carthamus Tinctorius* Oil, *Helianthus Annuus* Seed Oil, synthetic oils and extracts thereof and mixtures thereof.

2. The product of claim 1 further comprises methyl sulfonyl methane.

3. The product of claim 1 further comprises lactoferrin.

4. The product of claim 1 further comprises at least one aromatherapeutical substance, said aromatherapeutical substance is selected from a group consisting of *Lavendula Angustifolia* oil, *Geranium Maculatum* Oil, *Citrus Grandis* oil, *Juniperus Communis* Oil, *Pimenta Acris* Oil, *Lavendula Hybrida, Geranium Robertianum, Gernium Thunbergil, Citrus Aurantium Dulsis* Oil, *Citrus Nobilis* Oil, *Citrus Limonum* Oil and extracts thereof and mixtures thereof.

5. The product of claim 1 further comprises at least one skin nourishing/wound healing substance, said skin nourishing/wound healing substance is selected from a group consisting of aloe barbadensis leaf juice, white willow bark, and extracts thereof and mixtures thereof.

6. The product of claim 1 further comprises at least one active drug.

7. The product of claim 6 wherein said active drug is salicylic acid.

8. The product of claim 1 further comprises at least one muscle soothing substance, said muscle soothing substance is selected from a group consisting of Menthol, *Methyl Salicylate, Eucalyptus Globulus* Oil, Camphor, and *Mentha Piperita* Oil and extracts thereof and mixtures thereof.

9. A skin care formulation comprising at least one whole egg, at least one humectant substance, at least one emollient substance, and methyl sulfonyl methane, said whole egg being selected from a group consisting of chicken eggs, reptile eggs and mixtures thereof, said whole egg having water extracted from it, said humectant substance is selected from a group consisting of glycerin, butylenes glycol, propylene glycol, pentylene glycol and mixtures thereof, said emollient substance is selected from a group consisting of *Prunus Amygdalus Dulcis* Oil, Squalene, *Prunus Armeniaca* Kernel Oil, *Carthamus Tinctorius* Oil, *Helianthus Annuus* Seed Oil, synthetic oils and extracts thereof and mixtures thereof.

10. A skin care formulation comprising at least one whole egg, at least one humectant substance, at least one emollient substance, lactoferrin, said whole egg being selected from a group consisting of chicken eggs, reptile eggs and mixtures thereof, said whole egg having water extracted from it, said humectant substance is selected from a group consisting of glycerin, butylenes glycol, propylene glycol, pentylene glycol and mixtures thereof, said emollient substance is selected from a group consisting of *Prunus Amygdalus Dulcis* Oil, Squalene, *Prunus Armeniaca* Kernel Oil, *Carthamus Tinctorius* Oil, *Helianthus Annuus* Seed Oil, synthetic oils and extracts thereof and mixtures thereof.

11. The formulation of claim 10 further comprises methyl sulfonyl methane.

12. The product of claim 1 wherein said whole egg comprises water-soluble egg.

13. The product of claim 9 further comprises at least one aromatherapeutical substance, said aromatherapeutical substance is selected from a group consisting of *Lavendula Angustifolia* oil, *Geranium Maculatuxn* Oil, *Citrus Grandis* oil, *Juniperus Communis* Oil, *Pimenta Acris* Oil, *Lavendula Hybrida, Geranium Robertianum, Geranium Thunbergil, Citrus Aurantium Dulsis* Oil, *Citrus Nobilis* Oil, *Citrus Limonum* Oil and extracts thereof and mixtures thereof.

14. The product of claim 9 further comprises at least one skin nourishing/wound healing substance, said skin nourishing/wound healing substance is selected from a group consisting of aloe barbadensis leaf juice, white willow bark, and extracts thereof and mixtures thereof.

15. The product of claim 9 further comprises at least one active drug.

16. The product of claim 9 further comprises at least one muscle soothing substance, said muscle soothing substance is selected from a group consisting of Menthol, *Methyl Salicylate, Eucalyptus Globulus* Oil, Camphor, and *Mentha Piperita* Oil and extracts thereof and mixtures thereof.

17. The product of claim 10 further comprises at least one aromatherapeutical substance, said aromatherapeutical substance is selected from a group consisting of *Lavendula Angustifolia* oil, *Geranium Maculatum* Oil, *Citrus Grandis* oil, *Juniperus Communis* Oil, *Pimenta Acris* Oil, *Lavendula Hybrida, Geranium Robertianuni, Geranium Thunbergil, Citrus Aurantium Dulsis* Oil, *Citrus Nobilis* Oil, *Citrus Limonum* Oil and extracts thereof and mixtures thereof.

18. The product of claim 10 further comprises at least one skin nourishing/wound healing substance, said skin nourishing/wound healing substance is selected from a group consisting of aloe barbadensis leaf juice, white willow bark, and extracts thereof and mixtures thereof.

19. The product of claim 10 further comprises at least one active drug.

20. The product of claim 10 further comprises at least one muscle soothing substance, said muscle soothing substance is selected from a group consisting of Menthol, *Methyl Salicylate, Eucalyptus Globulus* Oil, Camphor, and *Mentha Piperita* Oil and extracts thereof and mixtures thereof.

* * * * *